US012735646B2

(12) United States Patent
Ali et al.

(10) Patent No.: US 12,735,646 B2
(45) Date of Patent: Sep. 15, 2026

(54) PRODUCTION OF MONOAROMATIC HYDROCARBONS FROM HYDROCARBON FEEDSTOCKS

(71) Applicants: SABIC Global Technologies B.V., Bergen op Zoom (NL); King Fahd University of Petroleum and Minerals, Dhahran (SA)

(72) Inventors: Syed Ahmed Ali, Dhahran (SA); Ziyauddin Shahabuddin Qureshi, Dhahran (SA); Khalid Jafar Al-Nawad, Dhahran (SA); Abdullah Mohammed Aitani, Dhahran (SA); Sulaiman Saleh Al-Khattaf, Dhahran (SA); Abdulkarim Al-Mutairi, Riyadh (SA); Khalid Almajnouni, Riyadh (SA); Nabil Alyasser, Riyadh (SA); Mahalingam Rathinam Jothi, Riyadh (SA)

(73) Assignees: SABIC GLOBAL TECHNOLOGIES B.V., Bergen op Zoom (NL); King Fahd University of Petroleum and Minerals, Dhahran (SA)

( * ) Notice: Subject to any disclaimer, the term of this patent is extended or adjusted under 35 U.S.C. 154(b) by 310 days.

(21) Appl. No.: 18/283,535

(22) PCT Filed: Mar. 17, 2022

(86) PCT No.: PCT/EP2022/056966

§ 371 (c)(1),
(2) Date: Sep. 22, 2023

(87) PCT Pub. No.: WO2022/200164

PCT Pub. Date: Sep. 29, 2022

(65) Prior Publication Data

US 2024/0182796 A1 Jun. 6, 2024

(30) Foreign Application Priority Data

Mar. 24, 2021 (EP) .................................... 21164478

(51) Int. Cl.

| | |
|---|---|
| ***C10G 47/00*** | (2006.01) |
| ***B01J 29/16*** | (2006.01) |
| ***B01J 29/74*** | (2006.01) |
| ***B01J 29/78*** | (2006.01) |
| ***B01J 35/63*** | (2024.01) |
| ***B01J 35/64*** | (2024.01) |
| ***C10G 47/20*** | (2006.01) |

(52) U.S. Cl.

CPC ............ *C10G 47/20* (2013.01); *B01J 29/166* (2013.01); *B01J 29/7415* (2013.01); *B01J 29/7815* (2013.01); *B01J 35/633* (2024.01); *B01J 35/647* (2024.01); *B01J 2229/18* (2013.01); *C07C 2523/28* (2013.01); *C07C 2523/42* (2013.01); *C07C 2523/75* (2013.01); *C07C 2523/755* (2013.01); *C07C 2529/16* (2013.01); *C07C 2529/74* (2013.01); *C07C 2529/78* (2013.01)

(58) Field of Classification Search

CPC ........ C10G 45/64; C10G 47/20; C10G 47/18; B01J 35/633; B01J 35/647; B01J 29/7415; B01J 29/076; B01J 29/166; B01J 29/7815; B01J 29/068; B01J 2229/18; C07C 2523/755; C07C 2523/42; C07C 2523/28; C07C 2523/75; C07C 2529/78; C07C 2529/16; C07C 2529/74

See application file for complete search history.

(56) References Cited

U.S. PATENT DOCUMENTS

| | | | |
|---|---|---|---|
| 4,857,171 | A | 8/1989 | Hoek et al. |
| 5,321,177 | A | 6/1994 | Nakamura et al. |
| 5,393,410 | A | 2/1995 | Habib et al. |
| 7,462,276 | B2 | 12/2008 | Wang et al. |
| 7,513,988 | B2 | 4/2009 | Oballa et al. |

(Continued)

FOREIGN PATENT DOCUMENTS

| | | | |
|---|---|---|---|
| CN | 104923290 | A | 9/2015 |
| CN | 107286989 | A | 10/2017 |

(Continued)

OTHER PUBLICATIONS

Dicyclopentadiene, Safety Data Sheet, Nova Chemicals (Year: 2024).*

Anderson et al.; "Western, Retained and Desorbed Products from Reaction of 1-Hexene over H-ZSMS Zeolite: Routes to Coke Precursors"; Journal of Catalysis, vol. 118; 1989; pp. 466-482.

Ardakani et al; "Hydrogenation and ring opening of naphthalene on bulk and supported Mo2C catalysts"; Applied Catalysis A: General; vol. 324; 2007; pp. 9-19.

Belohlav et al.; "Kinetic Model for Dicyclopentadiene Monomeration Process"; Chemical and Biochemical Engineering Quarterly, 14; 2000; pp. 29-34.

(Continued)

*Primary Examiner* — Prem C Singh
*Assistant Examiner* — Brandi M Doyle
(74) *Attorney, Agent, or Firm* — CANTOR COLBURN LLP

(57) ABSTRACT

A process for converting a feedstock including dicyclopentadiene to monoaromatic hydrocarbons, the process including providing a hydrocracking catalyst including a zeolite support having an average pore diameter of 5 to 13 nanometers, such as 9 to 12 nanometers, and greater than 3 to 15 weight percent, such as 5 to 15 weight percent of molybdenum tungsten, nickel, cobalt, platinum, palladium, or a combination comprising at least one of the foregoing impregnated on the zeolite support based on a total weight of the hydrocracking catalyst; and contacting the feedstock with the hydrocracking catalyst in the presence of hydrogen to provide a reaction product stream including the monoaromatic hydrocarbons converted from the dicyclopentadiene.

14 Claims, No Drawings

(56) References Cited

U.S. PATENT DOCUMENTS

| | | | |
|---|---|---|---|
| 9,446,997 B2 | 9/2016 | Yanagawa et al. | |
| 9,919,293 B1 | 3/2018 | Rana et al. | |
| 10,358,612 B2 | 7/2019 | Pelaez | |
| 10,953,396 B2 | 3/2021 | Sun et al. | |
| 2008/0051615 A1 | 2/2008 | Stavens et al. | |
| 2010/0087692 A1 | 4/2010 | Yoshimura et al. | |
| 2013/0184506 A1 | 7/2013 | Yanagawa et al. | |
| 2015/0275103 A1 | 10/2015 | Yanagawa et al. | |
| 2021/0130714 A1* | 5/2021 | Abudawoud | C10G 45/44 |

FOREIGN PATENT DOCUMENTS

| | | |
|---|---|---|
| EP | 0247678 B1 | 2/1990 |
| JP | 2007154151 A | 6/2007 |
| KR | 20160029972 A | 3/2016 |
| KR | 101621290 B1 | 5/2016 |
| KR | 101941952 B1 | 1/2019 |
| WO | 2013182534 A1 | 12/2013 |
| WO | 2015000841 A1 | 1/2015 |
| WO | 2017055095 A1 | 4/2017 |
| WO | 2017055096 A1 | 4/2017 |
| WO | 2017055097 A1 | 4/2017 |
| WO | 2017055098 A1 | 4/2017 |
| WO | 2017144438 A1 | 8/2017 |
| WO | 2017148735 A1 | 9/2017 |
| WO | 2018236709 A1 | 12/2018 |
| WO | 2019186368 A1 | 10/2019 |
| WO | 2019197987 A1 | 10/2019 |

OTHER PUBLICATIONS

Choi, et al.; "APU technology for the production of BTX and LPG from pyrolysis gasoline using metal promoted zeolite catalyst"; Catalysis Surveys from Asia, vol. 10, No. 2; 2006; pp. 110-116.

Dow Chemicals; "Dicyclopentadiene Products—A guide to product handling and use"; pp. 1-30.

Gonzalez; "The impact of Saudi ethane price increases on competitiveness"; 2016; Retrieved from http://blogs.platts.com/2016/01/19/saudi-ethane-price-competitiveness/.

International Search Report for International Application No. PCT/EP2022/056966; International Filing Date Mar. 17, 2022; Date of Mailing Jun. 15, 2022; 4 pages.

Mercier Des Rochettes et al.; "Coke formation mechanism from olefins or diolefins, under catalytic cracking conditions"; B. Delmon and G.F. Froment (Editors), Catalyst Deactivation, Elsevier Science Publishers B.V.; 1987; pp. 589-603.

Sato et al.; "Aromatic compounds synthesis from cyclopentadiene"; Applied Catalysis A: General 111; 1994; pp. 1-9.

Sibi et al; "Single-step catalytic liquid-phase hydroconversion of DCPD into high energy density fuel exo-THDCPD"; Green Chem., vol. 14; 2012; pp. 976-983.

Skala et al.; "Kinetics of DCPD hydrogenation using Pd/C catalyst"; Petroleum and Coal, vol. 45, 3-4; 2003; pp. 105-108.

Upare et al.; "Cobalt promoted Mo/beta zeolite for selective hydrocracking of tetralin and pyrolysis fuel oil into monocyclic aromatic hydrocarbons"; J. Ind. Eng. Chem., vol. 35; 2016; pp. 99-107.

Upare et al.; "Selective hydrocracking of pyrolysis fuel oil into benzene, toluene and xylene over CoMo/beta zeolite catalyst"; J. Ind. Eng. Chem., vol. 46; pp. 356-363.

Written Opinion for International Application No. PCT/EP2022/056966; International Filing Date Mar. 17, 2022; Date of Mailing Jun. 15, 2022; 6 pages.

* cited by examiner

PRODUCTION OF MONOAROMATIC HYDROCARBONS FROM HYDROCARBON FEEDSTOCKS

CROSS-REFERENCE TO RELATED APPLICATIONS

This application is a National Stage application of PCT/EP2022/056966, filed Mar. 17, 2022, which claims the benefit of European Application No. 21164478.6, filed Mar. 24, 2021, both of which are incorporated by reference in their entireties herein.

BACKGROUND

Catalytically cracking olefin feedstock hydrocarbons can produce a multitude of hydrocarbons (e.g., $C_{5+}$ alkenes; lower alkenes such as ethylene and propylene; $C_4$ alkanes; and fuel gas). A portion of the naphtha cracker product can be in liquid form, which can include pyrolysis gasoline (e.g., including benzene, toluene, and xylenes) and pyrolysis oil (e.g., including $C_{9+}$ hydrocarbons). Pyrolysis gasoline (PyGas) can be hydrogenated by a one- or two-stage hydrotreatment to remove diolefins, olefins, and sulfur. The hydrogenated PyGas can be blended into gasoline or fractionated to recover higher value BTX (benzene, toluene, and xylenes). The raffinate or pyrolysis oil (PyOil), which contains heavier ($C_{9+}$) hydrocarbons, may generally be disposed of as low-value fuel oil.

An interest exists for converting hydrocarbon feedstocks (e.g., feedstocks including $C_{9+}$ hydrocarbons, such as dicyclopentadiene) to monoaromatic hydrocarbons (e.g., BTX).

These and other inefficiencies and opportunities for improvement are addressed by the processes, methods, and catalysts of the present disclosure.

BRIEF DESCRIPTION

The present disclosure provides improved processes, methods, and catalysts for converting hydrocarbon feedstocks (e.g., feedstocks, such as PyOil, including $C_{9+}$ hydrocarbons, such as dicyclopentadiene and derivatives thereof) to monoaromatic hydrocarbons (e.g., BTX). More particularly, the present disclosure provides, in various aspects, advantageous processes for selectively converting $C_{9+}$ hydrocarbons (e.g., dicyclopentadiene) to high-value monoaromatic hydrocarbons (e.g., BTX).

The present disclosure provides a process for converting a feedstock including dicyclopentadiene to monoaromatic hydrocarbons by providing a hydrocracking catalyst including a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst; and contacting the feedstock with the hydrocracking catalyst in the presence of hydrogen to provide a reaction product stream including the monoaromatic hydrocarbons converted from the dicyclopentadiene. The feedstock and the reaction product stream can include indene or a derivative thereof, naphthalene or a derivative thereof, or a combination comprising at least one of the foregoing.

The present disclosure also provides a process for converting a feedstock including dicyclopentadiene to monoaromatic hydrocarbons by contacting the feedstock with a hydrocracking catalyst in the presence of hydrogen in a hydrocracking reaction zone at a pressure of 500 to 3,500 kilopascals, a temperature of 200 to 500° C., and a liquid hourly space velocity of 0.5 to 6 hour“1, such as a pressure of 1,000 to 3,000 kilopascals, a temperature of 250 to 450° C., and a liquid hourly space velocity of 1 to 5 $hour^{-1}$, or a pressure of 1,500 to 2,500 kilopascals, a temperature of 300 to 400° C., and a liquid hourly space velocity of 2 to 4 hour’", to convert at least a portion of the dicyclopentadiene to monoaromatic hydrocarbons, and provide an intermediate product stream including the monoaromatic hydrocarbons converted from the dicyclopentadiene, indene or a derivative thereof, naphthalene or a derivative thereof, or a combination comprising at least one of the foregoing, wherein the hydrocracking catalyst includes a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst. The process further includes contacting at least a portion of the intermediate product stream with a selective ring opening catalyst in the presence of hydrogen in a selective ring opening reaction zone at a pressure of 1,000 to 15,000 kilopascals and at a temperature of 100 to 700° C., such as 3,000 to 13,000 kilopascals and 200 to 600° ° C. or 5,000 to 10,000 kilopascals and 300 to 500° C., to convert at least a portion of the indene or a derivative thereof, naphthalene or a derivative thereof, or a combination comprising at least one of the foregoing to additional monoaromatic hydrocarbons, wherein the selective ring opening catalyst includes a zeolite support having a silica to alumina molar ratio of 25 to 100, such as 30 to 45, 33 to 42, or 35 to 40, and 0.01 to 20 weight percent, such as 0.05 to 18 weight percent or 0.1 to 15 weight percent, of a metal impregnated on the zeolite support of the selective ring opening catalyst, based on a total weight of the selective ring opening catalyst, wherein the metal includes molybdenum, tungsten, nickel, cobalt, platinum, palladium, or a combination comprising at least one of the foregoing.

The present disclosure further provides an integrated process for converting a feedstock including dicyclopentadiene to monoaromatic hydrocarbons by contacting the feedstock with a hydrocracking catalyst in the presence of hydrogen in a hydrocracking reaction zone at a pressure to convert at least a portion of the dicyclopentadiene to monoaromatic hydrocarbons, and provide an intermediate product stream including the monoaromatic hydrocarbons converted from the dicyclopentadiene, indene or a derivative thereof, naphthalene or a derivative thereof, or a combination comprising at least one of the foregoing, wherein the hydrocracking catalyst includes a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst; and contacting at least a portion of the intermediate product stream with a selective ring opening catalyst in the presence of hydrogen in a selective ring opening reaction zone to convert at least a portion of the indene or a derivative thereof, naphthalene or a derivative thereof, or a combination comprising at least one of the foregoing to additional monoaromatic hydrocarbons, wherein the hydrocracking reaction zone and the selective ring opening reaction zone are within a single reactor.

The above described and other features are exemplified by the following detailed description.

Any combination or permutation of aspects is envisioned. Additional advantageous features, functions and applications of processes, methods, and catalysts of the present disclosure will be apparent from the description which follows.

DETAILED DESCRIPTION

Aspects disclosed herein are illustrative of advantageous processes for selectively converting hydrocarbon feedstocks (e.g., feedstocks including $C_{9+}$ hydrocarbons, such as dicyclopentadiene) to high-value monoaromatic hydrocarbons (e.g., BTX). It should be understood, however, that disclosed aspects are merely exemplary of the present disclosure, which may be embodied in various forms. Therefore, details disclosed herein with reference to exemplary processes are not to be interpreted as limiting.

The present disclosure provides advantageous processes for selectively converting hydrocarbon feedstocks (e.g., feedstocks, such as PyOil, including $C_{9+}$ hydrocarbons, such as dicyclopentadiene and derivatives thereof) to high-value monoaromatic hydrocarbons (e.g., BTX). The processes of the present disclosure can improve dicyclopentadiene conversion as well as monoaromatic hydrocarbon (MAH) Yield, MAH Selectivity, BTX yield, BTX Selectivity, or a combination comprising at least one of the foregoing.

Compared to dicyclopentadiene and derivatives thereof, indene and derivatives thereof and naphthalene and derivatives thereof are relatively stable and may require severe conditions for selective ring opening. It is noted that when a suitable catalyst and severe process conditions are used for direct simultaneous conversion of dicyclopentadiene and derivatives thereof, indene and derivatives thereof, and naphthalene and derivatives thereof, undesirable reactions of dicyclopentadiene and derivatives thereof (e.g., formation of undesired cycloalkanes and $C_{1-4}$ gaseous hydrocarbons) can occur. Accordingly, it can be difficult to achieve high conversion of $C_{9+}$ hydrocarbons (e.g., dicyclopentadiene and derivatives thereof, indene and derivatives thereof, and naphthalene and derivatives thereof) in a hydrocarbon feedstock as well as high selectivity to monoaromatic hydrocarbons. Desired is a maximum conversion of dicyclopentadiene and derivatives thereof to monoaromatic hydrocarbons while minimizing or preventing the formation of undesired cycloalkanes and $C_{1-4}$ gaseous hydrocarbons, and maintaining a high conversion of $C_{9+}$ hydrocarbons.

The present disclosure provides that it was surprisingly discovered that two-stage processing of a hydrocarbon feedstock including dicyclopentadiene improves overall conversion as well as yield of and selectivity towards MAH and BTX. A hydrocracking stage converts dicyclopentadiene and derivatives thereof and produces monoaromatic hydrocarbons; followed by a selective ring opening stage to convert indene and derivatives thereof and naphthalene and derivatives thereof and increase the amount of MAH and BTX and maximize MAH and BTX content.

The term "$C_n$" hydrocarbon wherein n is a positive integer, e.g., 1, 2, 3, 4, 5, 6, 7, 8, 9, 10, 11, 12, as used herein means a hydrocarbon having n number of carbon atom(s) per molecule. The term "$C_{n+}$" hydrocarbon wherein n is a positive integer, e.g., 1, 2, 3, 4, 5, 6, 7, 8, 9, 10, 11, 12, as used herein means a hydrocarbon having n or more carbon atom(s) per molecule.

An exemplary feedstock, e.g., a hydrocarbon feedstock, includes $C_{9+}$ hydrocarbons, but can vary in the amount based on the feedstock source(s). For example, the hydrocarbon feedstock can be a PyOil, which can be produced from byproducts (for example $C_{9+}$ hydrocarbon fractions of catalytic reforming and steam cracking for ethylene/propylene production) of processes such as catalytic reforming, steam cracking, or pyrolysis for ethylene/propylene production. Pyrolysis oil can be a synthetic, liquid, non-fossil fuel product, produced by the pyrolysis (e.g., thermal decomposition and destructive distillation) of biomass, which is biological material derived from living or recently living organisms. When derived from a biomass, pyrolysis oil is also known as biomass pyrolysis oil, bio-oil, biocrude, biocrude oil, bioleum, wood pyrolysis oil, wood oil, liquid wood, biomass pyrolysis liquid, or pyroligeneous tar. Pyrolysis oil can also be obtained from non-biomass source through non-biomass substrates such as rubber tires, thermoplastics (including post-consumer plastics), and auto fluff. PyOil can also be obtained from mixed waste plastics through pyrolysis.

The exact characteristics and composition of the pyrolysis oil can vary depending on the method of pyrolysis performed and the nature of the feedstock. For example, the pyrolysis oil can include aliphatic hydrocarbons having five or more carbon atoms (e.g., 2-methylpentene), naphthenes, olefins, $C_8$ aromatic hydrocarbons such as ethylbenzene, Cy aromatic hydrocarbons (e.g., para-ethyltoluene, meta-ethyltoluene ortho-ethyltoluene, pseudocumene, mesitylene, hemimellitene, n-propylbenzene, indane, a combination comprising at least one of the foregoing, or the like), BTX (benzene, toluene, xylenes), dicyclopentadiene and derivatives thereof (e.g., dihydrodicyclopentadiene, methyldicyclopentadiene, tetrahydrodicyclopentadiene, dimethyldicyclopentadiene, hexahydro-4,7-methanoindene, or the like), polyaromatic hydrocarbons including $C_{9+}$ aromatic hydrocarbons, for example indene and derivatives thereof (e.g., methylindene, octahydro-4,7-methanoindene, or the like), naphthalene and derivatives thereof (e.g., methylnaphthalene, dihydronaphthalene, dimethylnaphthalene, phenylnapthalene, butyltetrahydronaphthalene, dimethyltetrahydronaphthalene, methyldecahydronaphthalene, trimethyldihydronaphthalene, or the like), or a combination comprising at least one of the foregoing. Other hydrocarbons that can be present include, but are not limited to, methylcyclopentene, methylphenylcyclopentane, 1,3-cyclohexadiene, isopropylmethylcyclohexane, dimethyl-1,3-cyclopentadiene, phenylacetylene, styrene, ethyltoluene, allylbenzene, n-propylbenzene, α-methylstyrene, propenylbenzene, cyclohexylbenzene, cyclopentylbenzene, dimethylhexenyl benzene, methylhexenylbenzene, trimethylbenzenes such as mesitylene (1,3,5-trimethylbenzene), hemimellitene (1,2,3-trimethylbenzene), and pseudocumene (1,2,4-trimethylbenzene), tetramethylbenzene such as durene (1,2,4,5-tetramethylbenzene), vinyltoluene, indane, tricyclodecene, bicyclododecene, tricycloundecene, methyltricyclodecene, methyltricycloundecene, phenylbutene, ethyltricyclodecene, ethyl/endo-tricyclodecane, 3-methyl-exo/endo-tricyclodecane, 2-methyl-trans-decalin, pentylbicycloheptane, biphenyl, 2-phenylnorbornene, biphenylene, acenaphthene, fluorene, phenanthrene, terphenyl, or a combination comprising at least one of the foregoing.

The hydrocarbon feedstock can include any suitable amount of $C_{9+}$ hydrocarbons. For example, the hydrocarbon feedstock can include 10 to 95 weight percent (wt. %) of the $C_{9+}$ hydrocarbons, or 20 to 90 wt. % $C_{9+}$ hydrocarbons, or 30 to 85 wt. % $C_{9+}$ hydrocarbons, or 40 to 80 wt. % $C_{9+}$ hydrocarbons, based on the total weight of the hydrocarbon feedstock.

For example, the hydrocarbon feedstock can include $C_{9+}$ hydrocarbons that include, based on the total weight of the hydrocarbon feedstock, greater than 35 wt. %, such as greater than 40 wt. % or greater than 45 wt. % of dicyclopentadiene and derivatives thereof, such as 35 to 55 wt. %, or 35 to 50 wt. %, or 40 to 55 wt. %, or 40 to 50 wt. % of dicyclopentadiene and derivatives thereof; 10 to 30 wt. %, such as 10 to 25 wt. %, or 15 to 30 wt. %, or 15 to 25 wt. % of indene and derivatives thereof; and 5 to 20 wt. %, such as 5 to 16 wt. %, or 8 to 20 wt. %, or 8 to 16 wt. % of naphthalene and derivatives thereof.

In an aspect, the hydrocarbon feedstock can be PyOil including 40 to 55 wt. % dicyclopentadiene and derivatives thereof, 15 to 25 wt. % indene and derivatives thereof, 10 to 20 wt. % naphthalene and derivatives thereof, and 10 to 20 wt. % monoaromatic hydrocarbons.

As used herein, the phrases "and derivatives thereof" and "or a derivative thereof" refer to a derivative that can be present, e.g., in a given stream. The phrases "and derivatives thereof" and "or a derivative thereof" are not to suggest or imply that a derivative is necessarily present.

Heavy ($C_{10}$) aromatic hydrocarbons such as 4-mthyl indane, tetralin, or a combination comprising at least one of the foregoing can be formed from dicyclopentadiene by hydrocracking of the bridge-head C-C bond, followed by dehydrogenation, isomerization, hydrocracking, or a combination comprising at least one of the foregoing to form BTX as shown in the following reaction mechanism:

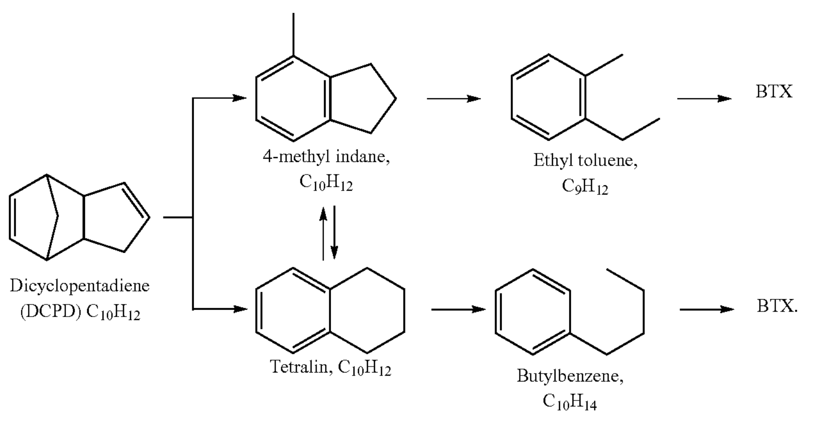

4-methyl indane, $C_{10}H_{12}$
Ethyl toluene, $C_9H_{12}$
Dicyclopentadiene (DCPD) $C_{10}H_{12}$
Tetralin, $C_{10}H_{12}$
Butylbenzene, $C_{10}H_{14}$ According to the reaction mechanism, monocyclic aromatic compounds can be formed through bicyclic intermediates by C-C bond scission of bicyclic compounds such as methylindane and tetralin, which can be derived by the bridge-head C-C bond fracture of dicyclopentadiene, rather than through cyclopentane and n-pentane. Selectivity to BTX can depend both on acidity of the zeolite and on the hydrogenation activity of metal impregnated on the zeolite.

In order to the increase the BTX yield, hydrocracking of the C-C bond of heavy aromatic hydrocarbons can be accelerated. Acid catalysis can be predominant under the conditions adopted.

In the presence of highly-reactive dicyclopentadiene, the conversion of indene and derivatives thereof and naphthalene and derivatives thereof can be difficult due to, for example, competitive adsorption and reactions. If strong catalyst and severe process conditions are applied for direct conversion of dicyclopentadiene as well as indene and derivatives thereof and naphthalene and derivatives, undesirable reactions of dicyclopentadiene and derivatives thereof can occur resulting in the formation of saturates and $C_{1-4}$ hydrocarbons. Accordingly, it can be difficult to achieve selective conversion of indene and derivatives thereof and naphthalene and derivatives in a hydrocarbon feedstock to monoaromatic hydrocarbons. An option to overcome this situation is to initially convert dicyclopentadiene and derivatives thereof in a hydrocarbon feedstock to mainly monoaromatic hydrocarbons and some indene and derivatives thereof.

Dicyclopentadiene, being a diene, is highly reactive component, which can react in a variety of ways. In contrast, indene and derivatives thereof and naphthalene and derivatives thereof are relatively stable and severe conditions may be appropriate for selective ring opening. In the presence of dicyclopentadiene, the conversion of indene and derivatives thereof and naphthalene and derivatives thereof can be difficult due to competitive adsorption and reactions. If strong catalyst and severe process conditions are applied for direct simultaneous conversion of dicyclopentadiene as well as indene and derivatives thereof and naphthalene and derivatives, undesirable reactions of dicyclopentadiene and derivatives thereof will occur. Accordingly, it can be difficult to achieve high conversion of $C_{9+}$ components of a hydrocarbon feedstock as well as high selectivity to monoaromatic hydrocarbons.

It was surprisingly discovered that dicyclopentadiene and derivatives thereof can first be converted into desirable products such as monoaromatic hydrocarbons and indene and derivatives thereof. Hence, a two-stage processing approach is proposed. In the first stage of the process, the catalyst and process conditions can be kept favorable for the maximum conversion of dicyclopentadiene and derivatives thereof. The first stage of the process can produce monoaromatic hydrocarbons and some increase in the amount of heavy aromatic hydrocarbons from the conversion of dicyclopentadiene.

The feed to the second stage of the process can include monoaromatic hydrocarbons, heavy aromatic hydrocarbons (such as indene and derivatives thereof, naphthalene and derivatives thereof, or a combination comprising at least one of the foregoing) and some saturated hydrocarbons. Relatively high hydrogen pressure and a temperature of 370 to 400° C. may provide desirable results for second stage of the process. Dicyclopentadiene and derivatives thereof present in the feed can be converted to saturated hydrocarbons or $C_{1-4}$ gaseous hydrocarbons. Hence, the content of dicyclopentadiene and derivatives thereof in the feed to the second stage of the process are desirably be as low as possible. The process conditions and catalyst for the second stage of the process are desirably aimed at selective ring opening of indene and derivatives thereof and naphthalene and derivatives thereof. Through such an approach, monoaromatic hydrocarbon yield can be maximized.

In a first stage of the process (e.g., hydrocracking) a desirable reaction is conversion of dicyclopentadiene and derivatives thereof to monoaromatic hydrocarbons as well as indene and derivatives thereof, naphthalene and derivatives thereof, or a combination comprising at least one of the foregoing. Undesirable reactions include conversion of dicyclopentadiene and derivatives thereof to nonaromatic hydrocarbons, $C_{1-4}$ hydrocarbons, or a combination comprising at least one of the foregoing and coke formation.

The hydrocracking can be conducted at a pressure of 1,000 to 15,000 kilopascals (kPa) and at a temperature of 100 to 700° C., such as 3,000 to 13,000 kPa and 200 to 600° C. or 5,000 to 10,000 kPa and 300 to 500° C. For example, hydrocracking can be carried by contacting the feedstock with a hydrocracking catalyst in the presence of hydrogen at a pressure of 500 to 3,500 kPa, a temperature of 200 to 500° C., and a liquid hourly space velocity (LHSV) of 0.5 to 6 $hour^{-1}$, such as a pressure of 1,000 to 3,000 kPa, a temperature of 250 to 450° C., and a LHSV of 1 to 5 $hour^{-1}$, or a pressure of 1,500 to 2,500 kPa, a temperature of 300 to 400° ° C., and a LHSV of 2 to 4 hour-1.

Taking into consideration the average critical diameter of aromatic hydrocarbons in the feedstock, a zeolite with desired pore cavity diameter and acidity can be appropriately selected. Zeolites such as mordenite, Y-zeolite, or β-zeolite, e.g., large-pore zeolites, can allow for relatively easy diffusion of dicyclopentadiene and derivates thereof and provide sufficient space to produce monoaromatic hydrocarbons by consecutive reactions of dehydrogenation and cracking, while excluding indene and derivatives thereof, naphthalene and derivatives thereof, or a combination comprising at least one of the foregoing. In an aspect, the zeolite can have an average pore diameter of 5 to 13 nanometers (nm), such as 9 to 12 nm. In an aspect, the zeolite includes Y-zeolite.

The hydrogenation activity and acidity of the hydrocracking catalyst can be controlled by appropriately selecting the type, amount, or a combination comprising at least one of the foregoing of metal to be impregnated on the zeolite. For example, the hydrocracking catalyst can include, for example, greater than 3 to 15 wt. %, such as 5 to 15 wt. %, of molybdenum, tungsten, nickel, cobalt, platinum, palladium, or a combination comprising at least one of the foregoing impregnated on a zeolite. In an aspect, the hydrocracking catalyst includes molybdenum impregnated on the zeolite. In an aspect, the hydrocracking catalyst can include molybdenum and nickel impregnated on the zeolite.

The metal can be incorporated onto the zeolite support of the hydrocracking catalyst by incipient wetness impregnation. The metal can be present on the surface of the zeolite support of the hydrocracking catalyst in the form of a metal oxide due to the incipient wetness impregnation. By contrast, metal incorporated by, for example, hydrothermal synthesis or ion exchange, would be present in cationic form.

The acidity of hydrocracking catalyst can be controlled by appropriately selecting the silica to alumina molar ratio of the zeolite. For example, the zeolite can have a silica to alumina molar ratio of 10 to 40, such as 15 to 40 or 15 to 35. The zeolite can have a total pore volume of less than 0.25 $cm^3/g$.

Desirably, conversion of dicyclopentadiene and derivatives thereof is maximized in, e.g., by, the hydrocracking. Desirably, yield and selectivity of monoaromatic hydrocarbons (MAH) is maximized in the hydrocracking. In an aspect, a conversion of dicyclopentadiene and derivates thereof in the feedstock is greater than each of a conversion of indene and derivatives thereof in the feedstock and a conversion of naphthalene and derivatives thereof in the feedstock. In an aspect, the hydrocracking further includes converting dicyclopentadiene to indene or a derivative thereof, naphthalene or a derivative thereof, or a combination comprising at least one of the foregoing.

In an aspect, the product of the hydrocracking can include the dicyclopentadiene and derivatives thereof in an amount of less than 5 wt. %, such as less than 3 wt. % or less than 1 weight wt. %, based on the total weight of the product of the hydrocracking. In an aspect, a conversion of dicyclopentadiene and derivates thereof in the hydrocracking is greater than 70 weight percent, such as greater than 75 weight percent or greater than 80 weight percent, based on a total weight of the dicyclopentadiene and derivatives thereof in the feedstock. In an aspect, the product of the hydrocracking can include less than 5 wt. % dicyclopentadiene and derivatives thereof, 20 to 30 wt. % indene and derivatives thereof, 20 to 25 wt. % naphthalene and derivatives thereof, 35 to 45 wt. % monoaromatic hydrocarbons, and 5 to 10 wt. % nonaromatic hydrocarbons and $C_{1-4}$ hydrocarbons.

In a second stage of the process (e.g., selective ring opening) indene and derivatives thereof and naphthalene and derivatives thereof in at least a portion of the product of the hydrocracking (e.g., a liquid portion of the product of the hydrocracking) are subject to ring opening. A desirable reaction is conversion of indene and derivatives thereof, naphthalene and derivatives thereof, or a combination comprising at least one of the foregoing to monoaromatic hydrocarbons. Undesirable reactions include formation of nonaromatic hydrocarbons, $C_{1-4}$ hydrocarbons, coke, or a combination comprising at least one of the foregoing.

The selective ring opening can be carried at a pressure of 1,000 to 15,000 kPa and at a temperature of 100 to 700° C., such as 3,000 to 13,000 kPa and 200 to 600° ° C. or 5,000 to 10,000 kPa and 300 to 500° C., to convert at least a portion of the indene or a derivative thereof, naphthalene or a derivative thereof.

Taking into consideration the average critical diameter of aromatic hydrocarbons in the feed to the selective ring opening reaction zone stock, a zeolite with desired pore cavity diameter and acidity can be appropriately selected. Zeolites such as Y-zeolite or β-zeolite, e.g., large-pore zeolites, can allow for relatively easy diffusion of $C_{9+}$ aromatic hydrocarbons and provide sufficient space to produce monoaromatic hydrocarbons. In an aspect, the zeolite includes β-zeolite.

The selective ring opening catalyst can include a zeolite having a silica to alumina ratio of 25 to 100, such as 30 to 45, 33 to 42, or 35 to 40. The selective ring opening catalyst can include 0.01 to 20 wt. %, such as 0.05 to 18 wt. % or 0.1 to 15 wt. %, of a metal impregnated on the zeolite, based on a total weight of the selective ring opening catalyst. The metal can include, for example, molybdenum, tungsten, nickel, cobalt, platinum, palladium, or a combination comprising at least one of the foregoing. In an aspect, the selective ring opening catalyst includes molybdenum or molybdenum and nickel.

Desirably, overall (e.g., following hydrocracking and selective ring opening) conversion of dicyclopentadiene and derivatives thereof as well as $C_{9+}$ hydrocarbons is maximized, with overall maximum yield and selectivity of monoaromatic hydrocarbons (MAH) and overall maximum yield and selectivity of BTX (benzene, toluene, and xylenes). In an aspect, overall conversion of dicyclopentadiene and derivatives thereof can be greater than 70 wt. %, such as greater than 80 wt. % or greater than 90 wt. %, based on a total weight of the dicyclopentadiene and derivates in the hydrocarbon feedstock. In an aspect, overall conversion of $C_{9+}$ hydrocarbons is greater than 60 wt. %, such as greater than 70 wt. % or greater than 80 wt. %, based on a total weight of the $C_{9+}$ hydrocarbons in the hydrocarbon feedstock.

The overall MAH yield and MAH selectivity are determined according to Equations 1 and 2 and the overall BTX yield and BTX selectivity are determined according to Equations 3 and 4:

$$MAH\ \text{Yield}(wt.\%)=100\times(MAH_{product}-MAH_{feedstock})/C_{9+feedstock} \quad \text{(Equation 1)}$$

$$MAH\ \text{Selectivity}\ (\%)=100\times MAH\ \text{Yield}(wt.\%)/\text{Conversion of}\ C_{9+}\text{hydrocarbons}(wt.\%) \quad \text{(Equation 2)}$$

$$BTX\ \text{Yield}(wt.\%)=100\times(BTX_{product}-BTX_{feedstock})/C_{9+feedstock} \quad \text{(Equation 3)}$$

$$BTX\ \text{Selectivity}\ (\%)=100\times BTX\ \text{Yield}(wt.\%)/\text{Conversion of}\ C_{9+}\text{hydrocarbons}(wt.\%) \quad \text{(Equation 4)}$$

wherein $MAH_{product}$ is the weight of monoaromatic hydrocarbons in the overall reaction product; MAH feedstock is the weight of monoaromatic hydrocarbons in the feedstock; $C_{9+\ feedstock}$ is the weight of $C_{9+}$ hydrocarbons (dicyclopentadiene and derivatives thereof, indene and derivatives thereof, and naphthalene and derivatives thereof) in the feedstock; Conversion of $C_{9+}$ hydrocarbons is the weight reduction (%) of $C_{9+}$ hydrocarbons; $BTX_{product}$ is the weight of BTX in the overall reaction product; and $BTX_{feedstock}$ is the weight of BTX in the feedstock.

In an aspect, overall MAH Yield can be greater than 10 wt. %, such as greater than 20 wt. % or greater than 30 wt. %. In an aspect, overall MAH Selectivity can be greater than 25%, such as greater than 30% or greater than 30%. In an aspect, overall BTX Yield can be greater than 15 wt. %, such as greater than 20 wt. % or greater than 25 wt. %. In an aspect, overall BTX Selectivity can be greater than 20%, such as greater than 25% or greater than 30%.

In an aspect, the product of the selective ring opening can include 60 to 70 wt. % monoaromatic hydrocarbons, less than 1 wt. % dicyclopentadiene and derivatives thereof, 20 to 30 wt. % nonaromatic hydrocarbons and $C_{1-4}$ hydrocarbons, less than 5 wt. % indene and derivatives thereof, and less than 5 wt. % naphthalene and derivatives thereof.

The product of the selective ring opening (e.g., the overall product) can be a physical mixture of different monoaromatic hydrocarbons or can be subjected to further separation, e.g., by distillation, to provide different purified product streams. Such purified product stream can include, for example, a benzene product stream, a toluene product stream, a xylene product stream, an ethylbenzene product stream, or a combination comprising at least one of the foregoing.

In an aspect, the hydrocracking reaction zone and the selective ring opening reaction zone can be contained within a single reactor. For example, within the single reactor, the hydrocracking reaction zone can be positioned above the selective ring opening reaction zone with an inert layer therebetween. Advantages of using a single reactor include simplified reactor set-up, lower capital expenditure, lower operating costs, and operation at constant temperature and pressure (e.g., without inter-stage compression and cooling/heating).

However, use of single reactor with the hydrocracking and selective ring opening catalysts loaded in layers can make the overall process less flexible in terms of process conditions and catalyst deactivation. For example, both stages may have to be operated at a same temperature and pressure. In an aspect in which the hydrocracking reaction zone and the selective ring opening reaction zone are contained within a single reactor, both the hydrocracking and the selective ring opening conditions can include, for example, a pressure of 1,000 to 15,000 kPa and at a temperature of 100 to 700° C., such as 3,000 to 13,000 kPa and 200 to 600° C. or 5,000 to 10,000 kPa and 300 to 500° C.

This disclosure is further illustrated by the following non-limiting examples.

EXAMPLES

The following examples are merely illustrative of processes for converting a feedstock including dicyclopentadiene to monoaromatic bydrocarbons disclosed herein and are not intended to limit the scope thereof.

Physical Measurements

Surface area, average pore diameter, and total pore volume measurements were carried out using a Micrometrics ASAP 2020 equipment (Norcross, GA, USA). Prior to the adsorption measurements, 0.05 grams (g) of the calcined catalyst sample was degassed under nitrogen flow for 3 hours (h) at 240° ° C. The adsorption isotherms were measured at −196° C. (liquid nitrogen temperature). The surface area, pore volume, and pore diameter were measured using Brunauer-Emmett-Teller (BET) or Barrett-Joyner-Halenda (BJH) adsorption calculation methods. Surface area can be measured according to ISO 9277 or ASTM D6556. Pore volume and pore diameter can be measured according to ISO 15901.

Acidity was measured by ammonia temperature programmed desorption ($NH_3$-TPD) using a chemisorption unit (BELCAT system). For each analysis, 0.1 g of the calcined catalyst sample was pretreated for 1 h at 500° C. using inert He (50 milliliters per minute (mL/min)). The catalyst was then exposed to He/$NH_3$ mixture in volume ratio of 95/5 volume percent (vol %) for 30 min at 100° C. Gaseous $NH_3$ was removed by purging using He for 1 h. The $NH_3$-TPD was performed using the same flow of He at a rate of 10° C./min up to 600° C. and the desorbed $NH_3$ was monitored using a thermal conductivity detector (TCD). The temperature at which $NH_3$ is desorbed is an estimation of acid site strength, e.g., higher the desorption temperature indicates a stronger acid site. The amount of acid sites is reported in millimoles per gram (mmol/g), based on the weight of the sample.

Gas chromatography was performed using an Agilent 5975C Gas Chromatograph-Mass Spectrometer and quantified using an Agilent 7890 Gas Chromatograph with a flame ionization detector (FID), employing an HP Innovax capillary column (60 m) with the oven temperature programmed from 75 to 250° C.

Hydrocracking Catalyst Preparation

A series of hydrocracking catalysts were synthesized using a wet impregnation method. Hexaammonium heptamolybdate tetrahydrate $(NH_4)Mo_7O_{24}.4H_2O$, nickel nitrate hexahydrate $Ni(NO_3)_2.6H_2O$, platinum chloride ($PtCl_2$) and ammonium metatungstate hydrate $(NH_4)_6H_2W_{12}O_{40}.xH_2O$ were used as metal precursors for incorporating molybdenum, nickel, platinum, and tungsten, respectively, in the hydrocracking catalyst. Appropriate quantities of metal precursor(s) and zeolite were added to 100 milliliters (mL) of water in a 250 mL round bottom flask and stirred with a magnetic stirrer (500 revolutions per minute (rpm)) for 1 h at room temperature to facilitate impregnation and obtain a homogenous mixture. Subsequently, water was removed in a rotary vapor under vacuum at 50° C. The impregnated hydrocracking catalyst was dried in air at 100° ° C. for 12 h to facilitate water evaporation. Then, the dried hydrocracking catalyst was calcined in air at 550° ° C. for 5 h to decompose and remove nitrate and provide the hydrocracking catalyst.

As an example, hydrocracking Catalyst B was prepared to contain 5 weight percent (wt. %) molybdenum metal supported on Y-zeolite ($SiO_2/Al_2O_3$ molar ratio: 15) by mixing 3.8 g of zeolite powder in H-form with 0.37 g of $(NH_4)_6M_{07}O_{24}{\cdot}4H_2O$ solution and stirring the mixture for 1 h at room temperature. Details of the hydrocracking catalysts can be found in Table 1.

TABLE 1

| Hydrocracking Catalyst | Support ($SiO_2/Al_2O_3$ molar ratio) | Metal(s) Impregnated | Surface Area ($m^2/g$) | Average Pore Diameter (nm) | Total Pore Volume ($cm^3/g$) |
|---|---|---|---|---|---|
| Comparative Example 1 | Pure Zeolite HY(15) | | 554 | 9.2 | 0.23 |
| Comparative Example 2 | Amorphous $SiO_2$—$Al_2O_3$ | Mo (10 wt. %) | | | |
| Catalyst A | Y-zeolite (10) | Mo (10 wt. %) | 649 | 8.6 | 0.19 |
| Catalyst B | Y-zeolite (15) | Mo (5 wt. %) | 513 | 9.6 | 0.22 |
| Catalyst C | Y-zeolite (15) | Mo (10 wt. %) | 408 | 10.3 | 0.23 |
| Catalyst D | Y-zeolite (15) | Mo (15 wt. %) | 337 | 11.6 | 0.21 |
| Catalyst E | Y-zeolite (15) | Mo (5 wt. %) + Ni (2 wt. %) | 460 | | |
| Catalyst F | Y-zeolite (15) | W (10 wt. %) | 458 | | |
| Catalyst G | Y-zeolite (30) | Mo (5 wt. %) | 568 | 5.9 | 0.23 |
| Catalyst H | Y-zeolite (30) | Mo (10 wt. %) | 509 | 6.0 | 0.24 |
| Catalyst I | Y-zeolite (40) | Mo (10 wt. %) | 319 | 6.7 | 0.19 |
| Catalyst J | β-zeolite (300) | Mo (10 wt. %) | 375 | | |

Physical Properties of Hydrocracking Catalysts

The surface area values of hydrocracking catalysts based on Y-zeolite were found to decrease after the metal impregnation. For hydrocracking catalysts based on Y-zeolite (15), greater molybdenum loading resulted in an increase in the average pore diameter, while the total pore volume changed only slightly. A similar trend was observed for hydrocracking catalysts based on Y-zeolite (30), which implies that most of the metal oxides over zeolites are uniformly deposited on the zeolite walls due to size-induced effects, which prevented migration and agglomeration of $MoO_3$ particles.

Hydrocracking Catalytic Performance

The performance of hydrocracking catalysts was evaluated in a fixed-bed flow reactor system. The reaction was carried out with pyrolysis oil (PyOil) as feedstock at 350° ° C. and 300 pounds per square inch (psi) (2,068 kilopascals (kPa)) hydrogen pressure.

The amount of hydrocracking catalyst loaded was 2 mL in a tubular reactor and the liquid hourly space velocity (LHSV) of the feed was maintained at 3 $h^{-1}$ (6 mL/h). Prior to the test, the hydrocracking catalyst was reduced under flowing hydrogen at 400° C. for 2 h. The hydrogen flow rate was kept constant at 50 mL/minute (min) during reduction and catalytic test. During the run, the liquid products were collected periodically and analyzed by gas chromatography (GC).

The results obtained are presented in terms of reaction product compositions, yields, and selectivities of monoaromatic hydrocarbons (MAH) and BTX (benzene, toluene, and xylenes).

Comparison of Hydrocracking (Stage I) Catalyst Performance

Generally hydrocracking catalysts supported on Y-zeolite with $SiO_2$—$Al_2O_3$ molar ratio of 15 or 10 exhibited higher conversion of dicyclopentadiene and derivatives thereof compared to hydrocracking catalysts prepared using other supports such as amorphous silica-alumina, Y-zeolite with greater (40) $SiO_2$—$Al_2O_3$ molar ratios or β-zeolite with $SiO_2$—$Al_2O_3$ molar ratio of 300. See Table 2.

Addition of 2 wt. % Ni (as in catalyst E) exhibited higher conversion of dicyclopentadiene and derivatives thereof but less monoaromatic hydrocarbons in the product. The increased hydrogenation due to addition of Ni can cause formation of more nonaromatic hydrocarbons. Tungsten does not seem to be a suitable active metal as more $C_{1-4}$ gas was formed—especially when supported over Y-zeolite.

TABLE 2

| Composition (wt. %) | Feed (PyOil) | Comparative Example 1 | Comparative Example 2 | Catalyst A | B | C | D | E | F | G | H | I | J |
|---|---|---|---|---|---|---|---|---|---|---|---|---|---|
| $C_{1-4}$ Alkanes | 0.00 | 4.71 | 5.51 | 8.45 | 6.70 | 7.23 | 7.07 | 8.06 | 12.50 | 5.20 | 4.20 | 3.80 | 6.22 |
| Benzene | 0.00 | 0.86 | 0.62 | 1.95 | 1.78 | 3.90 | 2.43 | 2.73 | 2.39 | 3.13 | 3.43 | 0.93 | 3.14 |
| Toluene | 1.64 | 1.92 | 0.47 | 2.37 | 1.17 | 3.42 | 1.75 | 2.28 | 3.63 | 3.19 | 3.39 | 0.67 | 3.28 |
| Xylenes | 1.22 | 2.03 | 2.80 | 4.25 | 3.88 | 4.10 | 3.80 | 3.35 | 2.58 | 4.46 | 4.80 | 4.47 | 4.82 |
| Ethylbenzene | 3.42 | 6.22 | 9.97 | 11.08 | 11.66 | 7.58 | 11.37 | 10.89 | 6.53 | 6.87 | 6.98 | 10.49 | 10.99 |
| n-Propylbenzene | 2.24 | 3.39 | 3.44 | 4.73 | 4.71 | 4.47 | 4.58 | 4.22 | 3.95 | 4.30 | 4.29 | 4.54 | 3.57 |
| i-Propylbenzene | 0.90 | 0.63 | 2.55 | 2.36 | 4.78 | 6.23 | 7.56 | 5.11 | 1.72 | 7.01 | 8.28 | 9.18 | 3.12 |
| Ethyl toluenes | 4.22 | 7.40 | 9.41 | 6.33 | 7.24 | 7.82 | 7.09 | 5.20 | 6.26 | 6.73 | 6.11 | 6.53 | 6.35 |
| Nonaromatic hydrocarbons (Saturates) | 1.48 | 9.04 | 3.92 | 10.90 | 1.77 | 8.98 | 6.48 | 9.19 | 7.52 | 14.32 | 17.32 | 3.16 | 13.90 |
| Dicyclopentadiene + derivatives thereof | 51.87 | 30.72 | 32.24 | 12.80 | 12.85 | 5.49 | 6.86 | 4.50 | 5.13 | 7.83 | 6.09 | 22.38 | 12.33 |
| Indene + derivatives thereof | 18.48 | 19.37 | 17.94 | 17.05 | 23.72 | 23.30 | 23.48 | 24.23 | 22.67 | 20.38 | 19.96 | 20.18 | 18.38 |
| Naphthalene + derivatives thereof | 14.53 | 13.72 | 11.14 | 17.74 | 19.74 | 17.48 | 17.52 | 20.23 | 25.11 | 16.57 | 15.15 | 13.66 | 13.90 |
| Grouped Amounts (wt. %) | | | | | | | | | | | | | |
| BTX | 2.86 | 4.80 | 3.90 | 8.58 | 6.82 | 11.42 | 7.99 | 8.35 | 8.60 | 10.78 | 11.62 | 6.07 | 11.24 |
| Monoaromatic hydrocarbons | 13.64 | 22.44 | 29.26 | 33.07 | 35.22 | 37.52 | 38.59 | 33.78 | 27.06 | 35.69 | 37.28 | 36.82 | 35.27 |
| Conversion (wt. %) | | | | | | | | | | | | | |
| Dicyclopentadiene + derivatives thereof | | 40.78 | 37.84 | 75.32 | 75.22 | 89.42 | 86.77 | 91.32 | 90.11 | 84.90 | 88.27 | 56.86 | 76.23 |

Selective Ring Opening Catalyst Preparation

A series of catalysts were synthesized using wet co-impregnation method for selective ring opening as listed in Table 3. The catalysts included β-zeolite having $SiO_2$—$Al_2O_3$ molar ratio of 25, 38, and 100 on which (i) molybdenum and nickel, (ii) molybdenum and cobalt, or (iii) platinum were impregnated.

Hexaammonium heptamolybdate tetrahydrate $(NH_4)_6Mo_7O_{24}.4H_2O$, nickel nitrate hexahydrate $Ni(NO_3)_2.6H_2O$, and platinum chloride ($PtCl_2$) were used a metal precursors for incorporating molybdenum, nickel, and platinum, respectively, in the catalyst. The selective ring opening catalysts were synthesized using a wet impregnation method. The procedures adopted for selective ring opening catalyst preparation are similar to those adopted for hydrocracking catalyst preparation. Details of the selective ring opening catalysts can be found in Table 3.

TABLE 3

| Selective Ring Opening Catalyst ($SiO_2/Al_2O_3$ molar ratio) | Support ($SiO_2/Al_2O_3$ molar ratio) | Metal(s) Impregnated | Surface Area ($m^2/g$) | Average Pore Diameter (nm) | Total Pore Volume ($cm^3/g$) |
|---|---|---|---|---|---|
| Comparative Example 3 | Pure Zeolite Hβ(38) | | 522 | 4.0 | 0.16 |
| Catalyst 2A | β-zeolite (38) | Mo (10 wt. %) + Ni (2 wt. %) | 375 | 5.6 | 0.14 |
| Catalyst 2B | β-zeolite (38) | Mo (20 wt. %) + Ni (4 wt. %) | | | |
| Catalyst 2C | β-zeolite (38) | Pt (1 wt. %) | | | |
| Catalyst 2D | β-zeolite (38) | Mo (10 wt. %) + Co (2 wt. %) | | | |
| Catalyst 2E | β-zeolite (25) | Mo (10 wt. %) + Ni (2 wt. %) | | | |
| Catalyst 2F | β-zeolite (100) | Mo (10 wt. %) + Ni (2 wt. %) | | | |

Hydrocracking and Selective Ring Opening Catalytic Performance

The performance of hydrocracking catalysts B, C, and D was evaluated in a fixed-bed flow reactor system. The reaction was carried out with PyOil as feedstock.

The process conditions for both hydrocracking and selective ring opening are listed in Table 4. Prior to the test, the catalyst was reduced at 400° C. for two hours under flowing hydrogen at 50 mL/min. During the run, the liquid products were collected periodically and analyzed by gas chromatography (GC).

TABLE 4

| Parameter | Hydrocracking | Selective Ring Opening |
|---|---|---|
| Feed | PyOil | Liquid Hydrocracking Product |
| Feed Flow Rate (mL/min) | 6 | 6 |
| Catalyst Volume (mL) | 2 | 2 |
| Temperature (° C.) | 350 | 370 |
| Hydrogen Pressure (psi) | 300 (2,068 kPa) | 900 (6,205 kPa) |
| LHSV ($h^{-1}$) | 3 | 3 |
| $H_2$ Flow Rate (mL/min) | 50 | 100 |

Comparison of Selective Ring Opening (Stage II) Catalyst Performance

Dicyclopentadiene and derivatives thereof are reduced in the hydrocracking product while indene and derivatives thereof and naphthalene and derivatives thereof are slightly increased. The selective ring opening product contains mostly monoaromatic hydrocarbons and nonaromatic hydrocarbons along with minor amounts of dicyclopentadiene and derivatives thereof, indene and derivatives thereof, and naphthalene and derivatives thereof.

Selective ring opening catalysts supported on β-zeolite with $SiO_2$—$Al_2O_3$ molar ratio of 38 exhibited higher conversion of indene and derivatives thereof and naphthalene and derivatives compared to β-zeolite with lower (25) or higher (100) $SiO_2$—$Al_2O_3$ molar ratios. See Tables 5-8.

The choice of metal(s) impregnated on β-zeolite with $SiO_2$—$Al_2O_3$ molar ratio of 38 also shows influence on the performance indices. Among the molybdenum containing catalysts, the formulations containing 10 wt. % molybdenum generally exhibited better performance. Addition of nickel as promoter improved the performance, while Co seems not to be effective. Use of 1 wt. % platinum resulted in higher BTX and monoaromatic hydrocarbons content in the product along with a higher conversion of $C_{9+}$ hydrocarbons.

Catalysts 2A and 2C performed better than the other selective ring opening catalysts. The conversion of indene and derivatives thereof and naphthalene and derivatives thereof was 80 to 97 wt. %. The final products have greater than 40 wt. % monoaromatic hydrocarbons including about 29 wt. % BTX. However, there was a substantial amount of nonaromatic hydrocarbons (34 wt. %) in addition to about 13 to 15 wt. % $C_{1-4}$ hydrocarbons.

TABLE 5

| | | Stage No. | | | | | |
|---|---|---|---|---|---|---|---|
| | | I | II | I | II | I | II |
| | PyOil | Catalyst | | | | | |
| Composition (wt. %) | (Feed) | C | 2A | B | 2B | D | 2C |
| $C_{1-4}$ Hydrocarbons | 0.00 | 0.00 | 12.83 | 5.00 | 16.70 | 0.00 | 14.50 |
| Benzene | 0.00 | 2.71 | 11.86 | 2.93 | 8.88 | 1.82 | 7.26 |
| Toluene | 1.64 | 2.58 | 9.81 | 3.25 | 8.58 | 1.39 | 12.54 |
| Xylenes | 1.22 | 4.08 | 6.88 | 2.56 | 4.50 | 3.38 | 8.80 |
| Ethylbenzene | 3.42 | 10.61 | 6.16 | 6.99 | 6.57 | 10.54 | 6.42 |
| n-Propylbenzene | 2.24 | 4.94 | 0.58 | 4.41 | 1.03 | 4.54 | 0.57 |
| i-Propylbenzene | 0.90 | 4.99 | 0.00 | 4.18 | 0.00 | 5.90 | 0.22 |
| Ethyl toluenes | 4.22 | 8.25 | 6.06 | 7.38 | 5.72 | 7.61 | 5.95 |
| Nonaromatic hydrocarbons (Saturates) | 1.48 | 6.59 | 34.41 | 10.62 | 34.11 | 6.68 | 34.42 |
| Dicyclopentadiene + derivatives thereof | 51.88 | 8.74 | 3.35 | 12.38 | 2.33 | 19.08 | 7.23 |
| Indene + derivatives thereof | 18.49 | 25.36 | 5.77 | 22.27 | 7.40 | 22.08 | 0.56 |
| Naphthalene + derivatives thereof | 14.53 | 21.14 | 2.30 | 18.03 | 4.20 | 16.98 | 1.53 |

TABLE 6

| | Overall (Stages I & II) using Catalysts C & 2A | Overall (Stages I & II) using Catalysts B & 2B | Overall (Stages I & II) using Catalysts D & 2C |
|---|---|---|---|
| Conversion (wt. %) | | | |
| Dicyclopentadiene + derivatives thereof | 93.54 | 95.51 | 86.06 |
| Indene + derivatives thereof | 68.79 | 59.98 | 96.97 |
| Naphthalene + derivatives thereof | 84.17 | 71.09 | 89.47 |
| Conversion of $C_{9+}$ hydrocarbons | 86.55 | 83.60 | 89.02 |
| Yield (wt. %) and Selectivity (%) | | | |
| MAH Yield | 32.63 | 25.48 | 33.13 |
| MAH Selectivity | 37.70 | 30.48 | 37.21 |
| BTX Yield | 30.26 | 22.49 | 30.32 |
| BTX Selectivity | 34.97 | 26.90 | 34.06 |

TABLE 7

| | | Stage No. | | | | | |
|---|---|---|---|---|---|---|---|
| | | I | II | I | II | I | II |
| | PyOil | Catalyst | | | | | |
| Composition (wt. %) | (Feed) | C | 2D | B | 2E | B | 2F |
| $C_{1-4}$ Hydrocarbons | 0.00 | 5.50 | 14.00 | 5.00 | 8.30 | 5.00 | 5.40 |
| Benzene | 0.00 | 4.34 | 6.04 | 2.52 | 7.38 | 3.13 | 7.12 |

TABLE 7-continued

| Composition (wt. %) | PyOil (Feed) | I C | II 2D | I B | II 2E | I B | II 2F |
|---|---|---|---|---|---|---|---|
| | | Stage No. / Catalyst | | | | | |
| Toluene | 1.64 | 5.87 | 11.42 | 2.35 | 4.37 | 3.47 | 8.53 |
| Xylenes | 1.22 | 4.85 | 5.77 | 2.9 | 2.83 | 2.73 | 4.29 |
| Ethylbenzene | 3.42 | 8.24 | 8.67 | 6.73 | 5.39 | 7.46 | 8.22 |
| n-Propylbenzene | 2.24 | 3.58 | 1.36 | 4.54 | 2.15 | 4.70 | 2.71 |
| i-Propylbenzene | 0.90 | 3.82 | 0.45 | 3.51 | 0.39 | 4.46 | 0.21 |
| Ethyl toluenes | 4.22 | 8.04 | 6.25 | 8.77 | 7.12 | 7.88 | 6.91 |
| Nonaromatic hydrocarbons (Saturates) | 1.48 | 16.72 | 29.80 | 8.06 | 35.32 | 5.77 | 30.81 |
| Dicyclopentadiene + derivatives thereof | 51.88 | 6.41 | 5.57 | 17.59 | 3.45 | 12.64 | 3.88 |
| Indene + derivatives thereof | 18.49 | 18.56 | 6.60 | 21.12 | 13.62 | 23.54 | 13.22 |
| Naphthalene + derivatives thereof | 14.53 | 14.07 | 4.07 | 16.80 | 9.69 | 19.22 | 8.71 |

TABLE 8

| | Overall (Stages I & II) using Catalysts C & 2D | Overall (Stages I & II) using Catalysts B & 2E | Overall (Stages I & II) using Catalysts B & 2F |
|---|---|---|---|
| Conversion (wt. %) | | | |
| Dicyclopentadiene + derivatives thereof | 89.26 | 93.35 | 92.52 |
| Indene + derivatives thereof | 64.31 | 26.34 | 28.50 |
| Naphthalene + derivatives thereof | 71.99 | 33.31 | 40.06 |
| Conversion of $C_{9+}$ hydrocarbons | 81.26 | 68.48 | 69.60 |
| Yield (wt. %) and Selectivity (%) | | | |
| MAH Yield | 31.00 | 18.84 | 28.67 |
| MAH Selectivity | 38.16 | 27.51 | 41.20 |
| BTX Yield | 24.00 | 13.79 | 20.12 |
| BTX Selectivity | 29.53 | 20.14 | 28.91 |

Loading of Catalysts in a Single Reactor

To determine the efficiency of loading the hydrocracking and selective ring opening catalysts in a single reactor in layers, tests were carried out by loading different catalysts in layers with 3 mL of hydrocracking catalyst on the top and 2 mL of selective ring opening catalyst in the bottom of the reactor tube with 1.0 mL of inert silicon carbide in the between the two layers. The tests were carried out at 360 ° C., 900 psi (6,205 kPa) of hydrogen pressure, feed flow rate of 6 mL/h, and hydrogen flow rate of 100 mL/min. Gaseous and liquid products were collected and analyzed. The liquid products were analyzed to identify and quantify the products.

A test was performed with pure zeolites HY(15) and Hβ(38) for the hydrocracking and selective ring opening stages without impregnation of metal to observe behavior towards the conversion of PyOil. Pure zeolites could convert only about 40 wt. % of $C_{9+}$ hydrocarbons present in the PyOil. See Table 9. The product contains about 33 wt. % monoaromatic hydrocarbons. A hydrogenating component of the catalyst (i.e., active metals) was not present, and the desired reactions for the formation of monoaromatic hydrocarbons did proceed to a desired extent. The addition of metals achieves higher conversion of $C_{9+}$ hydrocarbons and yield of monoaromatic hydrocarbons.

Five pairs of hydrocracking and selective ring opening catalysts were tested by loading in a single reactor in layers. The catalyst pairs are:

(i) hydrocracking Catalyst D and selective ring opening Catalyst 2A;

(ii) hydrocracking Catalyst D and selective ring opening Catalyst 2E;

(iii) hydrocracking Catalyst D and selective ring opening Catalyst 2G (β-zeolite (25) containing 8 wt. % Mo and 2 wt. % Ni);

(iv) hydrocracking Catalyst J and selective ring opening Catalyst 2A; and (v) hydrocracking Catalyst J and selective ring opening Catalyst 2G.

The conversion of $C_{9+}$ hydrocarbons was greater than 93 wt. % for the five pairs, with the highest conversion (98 wt. %) observed for hydrocracking Catalyst D and selective ring opening Catalyst 2E. The formation of monoaromatic hydrocarbons (59 wt. %) and BTX (36 wt. %) were also highest in the case of hydrocracking Catalyst D and selective ring opening Catalyst 2E. See Table 9.

Hydrocracking Catalyst D and selective ring opening Catalyst 2A can be considered as the benchmark. With the catalyst pair of hydrocracking Catalyst D and selective ring opening Catalyst 2A, the conversion of $C_{9+}$ hydrocarbons was 95.6 wt. %, which resulted in the 55.6 wt. % formation of monoaromatic hydrocarbons. The $C_{1-4}$ paraffins and $C_{5-6}$ cyclo-paraffins contents in the product were 21 wt. % and 20 wt. %, respectively. When the selective ring opening catalyst is changed from selective ring opening Catalyst 2A (based on β-zeolite (38)) to selective ring opening Catalyst 2E (based on β-zeolite (25)), a modest increase in the conversion of $C_{9+}$ hydrocarbons was observed, accompanied by higher $C_{1-4}$ paraffins, monoaromatic hydrocarbons and BTX formation. The slight reduction in $C_{5-6}$ cyclo-paraffins content is also noticed. The results can be attributed to the increased acidity of β-zeolite (25) compared to β-zeolite (38).

TABLE 9

| | Feed/Product Composition | PyOil | Catalysts: Comparative Catalyst 1 + Comparative Catalyst 3 | Catalyst D + Catalyst 2A | Catalyst D + Catalyst 2E | Catalyst D + Catalyst 2G | Catalyst J + Catalyst 2A | Catalyst J + Catalyst 2G |
|---|---|---|---|---|---|---|---|---|
| Paraffins | $C_1$ | 0.00 | 0.05 | 0.06 | 0.05 | 0.04 | 0.07 | 0.07 |
| | $C_2$ | 0.00 | 0.43 | 0.89 | 0.89 | 0.61 | 0.71 | 0.71 |
| | $C_3$ | 0.00 | 0.92 | 0.71 | 0.70 | 0.50 | 0.98 | 0.98 |
| | $C_4$ | 0.00 | 2.25 | 5.69 | 5.47 | 4.22 | 6.88 | 6.88 |
| | $C_5$ | 0.00 | 3.09 | 5.77 | 5.94 | 4.60 | 6.03 | 6.0 |
| | $C_{6+}$ | 0.00 | 3.76 | 7.78 | 9.40 | 9.95 | 10.08 | 10.08 |
| Cyclo-paraffins | Cyclopentanes | 0.95 | 3.70 | 15.31 | 10.59 | 15.37 | 14.36 | 14.36 |
| | Cyclohexanes | 0.53 | 2.09 | 4.44 | 6.29 | 9.30 | 9.20 | 9.20 |
| MAH | Benzene | 0.00 | 1.46 | 5.35 | 5.62 | 3.03 | 3.92 | 3.92 |
| | Toluene | 1.64 | 3.33 | 16.98 | 17.74 | 13.05 | 13.13 | 13.13 |
| | Ethylbenzene | 3.42 | 7.91 | 6.28 | 6.54 | 6.79 | 6.79 | 6.79 |
| | Xylenes | 1.22 | 2.91 | 11.91 | 12.44 | 8.45 | 8.02 | 8.02 |
| | Ethyltoluenes | 4.22 | 9.40 | 6.17 | 7.48 | 7.06 | 6.85 | 6.85 |
| | Propylbenzenes | 2.24 | 8.10 | 0.32 | 0.29 | 0.90 | 0.52 | 0.52 |
| | Trimethylbenzenes | 0.00 | 1.22 | 3.36 | 3.49 | 2.42 | 2.00 | 2.00 |
| | $C_{10+}$ aromatic hydrocarbons | 0.00 | 2.15 | 5.21 | 5.43 | 9.66 | 7.28 | 7.28 |
| Heavies | Dicyclopentadiene + derivatives thereof | 51.88 | 11.71 | 0.00 | 0.00 | 0.00 | 0.00 | 0.00 |
| | Indene + derivatives thereof | 18.49 | 19.47 | 1.59 | 1.37 | 3.48 | 2.73 | 2.73 |
| | Naphthalene + derivatives thereof | 14.53 | 19.43 | 2.18 | 0.27 | 0.56 | 0.45 | 0.45 |
| Grouped Amounts | | | | | | | | |
| | $C_{1-6+}$ Paraffins | 0.00 | 10.50 | 20.90 | 22.45 | 19.93 | 18.92 | 24.74 |
| | $C_{5-6}$ Cycloparaffins | 1.48 | 5.79 | 19.75 | 16.87 | 24.66 | 20.86 | 23.56 |
| | BTX | 2.86 | 7.70 | 34.24 | 35.80 | 24.53 | 22.93 | 25.07 |
| | MAH (total) | 13.64 | 33.11 | 55.58 | 59.03 | 51.37 | 54.06 | 48.52 |
| | Heavies | 84.89 | 50.60 | 3.77 | 1.64 | 4.04 | 6.17 | 3.18 |
| Conversion, Field, and Selectivity | | | | | | | | |
| | Conversion of $C_{9+}$ hydrocarbon (wt %) | — | 40.39 | 95.56 | 98.07 | 95.24 | 92.73 | 96.25 |
| | MAH Yield (wt %) | — | 22.93 | 49.40 | 53.47 | 44.45 | 47.61 | 41.09 |
| | MAH Selectivity (%) | — | 56.78 | 51.70 | 54.52 | 46.67 | 51.34 | 42.68 |

Comparing results using hydrocracking Catalyst D and selective ring opening Catalyst 2A, in two reactors 86.55 wt. % conversion of $C_{9+}$ hydrocarbons, 32.63 wt. % MAH Yield, and 37.70% MAH Selectivity were achieved, while in a single reactor 95.56 wt. % conversion of $C_{9+}$ hydrocarbons, 49.40 wt. % MAH Yield, and 51.70% MAH Selectivity were achieved.

When the selective ring opening catalyst is changed from selective ring opening Catalyst 2E (containing 10 wt. % Mo and 2 wt. % Ni) to selective ring opening Catalyst 2G (containing 8 wt. % Mo and 2 wt. % Ni), a modest (about 3 wt. %) decrease in the conversion of $C_{9+}$ hydrocarbons was observed, accompanied by a (8 wt. %) reduction in monoaromatic hydrocarbon formation. The BTX content also decreased by greater than 11 wt. %, accompanied by a (8 wt. %) increase in $C_{5-6}$ cyclo-paraffins content was observed. The results indicate that the catalyst selective ring opening Catalyst 2G does not possess sufficient hydrogenation activity to selectively produce monoaromatic hydrocarbons.

The next two tests were carried out using hydrocracking Catalyst J, which has Y-zeolite (30) as a support compared to Y-zeolite (15) as the support for hydrocracking Catalyst D. Due to the reduction of acidity of the hydrocracking catalyst, the product selectivity was affected. With the catalyst pair of hydrocracking Catalyst J and selective ring opening Catalyst 2A the conversion of $C_{9+}$ hydrocarbons was about 93 wt. %, which resulted in the formation of 54.1 wt. % monoaromatic hydrocarbons. The $C_{1-4}$ paraffins and $C_{5-6}$ cyclo-paraffins contents in the product were 19 wt. % and 21 wt. %, respectively, which are in the same range obtained with the catalyst pair of hydrocracking Catalyst D and selective ring opening Catalyst 2A. However, the BTX content (23 wt. %) from hydrocracking Catalyst J and selective ring opening Catalyst 2A was less than 34 wt. % obtained over the catalyst pair of hydrocracking Catalyst D and selective ring opening Catalyst 2A. The results indicate that higher acidity is desirable for the hydrocracking catalyst to effectively and selectively crack the $C_{9+}$ hydrocarbons.

When the hydrocracking catalyst is changed from selective ring opening Catalyst 2A (based on β-zeolite (38) and containing 10 wt. % Mo and 2 wt. % Ni) to selective ring opening Catalyst 2G (based on β-zeolite (25) containing 8 wt. % Mo and 2 wt. % Ni), a modest (3 wt. %) increase in the conversion of $C_{9+}$ hydrocarbons was observed, accompanied by a higher $C_{1-4}$ paraffins and $C_{5-6}$ cyclo-paraffins contents resulting in lower monoaromatic hydrocarbon formation. The results show the effect of increase in acidity of selective ring opening catalyst can cause over cracking and reduction in selective formation of monoaromatic hydrocarbons.

Table 10 presents the detailed analysis results of product obtained from hydrocracking Catalyst D and selective ring opening Catalyst 2E in a single reactor. The compounds are classified in groups as alkanes, cyclo-alkanes, monoaromatic hydrocarbons, and heavies (i.e., dicyclopentadiene and derivatives thereof, indene and derivatives thereof, and naphthalene and derivatives thereof). Many monoaromatic hydrocarbons are formed which were not detected in the GC analysis. Analysis shows higher monoaromatic hydrocarbons content due to addition of $C_{9+}$ aromatic hydrocarbons.

Among the monoaromatic hydrocarbons, toluene is present in the highest amount (about 18 wt. %) followed by xylenes (12.4 wt. %), ethyl benzene (6.5 wt. %) and benzene (5.6 wt. %). Among the cycloalkanes, methyl cyclopentane content was highest (8.8 wt. %), which was likely formed by the hydrocracking of dicyclopentadiene and derivatives thereof. Similarly, isopentane (4.5 wt. %) could also be formed by the ring opening of cyclopentanes. The heavies were unconverted indene and derivatives thereof and naphthalene and derivatives thereof.

TABLE 10

| Component | Mass % |
|---|---|
| Alkanes | |
| methane | 0.05 |
| ethane | 0.89 |
| propane | 0.70 |
| i-butane | 2.44 |
| n-butane | 3.03 |
| i-pentane | 4.50 |
| n-pentane | 1.44 |
| 2,2-dimethylbutane | 3.76 |
| 2-methylpentane | 1.81 |
| 3-methylpentane | 1.04 |
| n-hexane | 0.82 |
| 2-methylhexane | 0.21 |
| 3-methylhexane | 0.23 |
| 3-ethylpentane | 0.87 |
| 2,5-dimethylhexane | 0.66 |
| Total | 22.45 |
| Cycloalkanes | |
| methylcyclopentane | 8.83 |
| cyclohexane | 3.44 |
| 1,1-dimethylcyclopentane | 0.27 |
| 1c,3-dimethylcyclopentane | 0.91 |
| 1c,2-dimethylcyclopentane | 0.28 |
| methylcyclohexane | 2.32 |
| 1c,2t,4-trimethylcyclopentane | 0.30 |
| 1t,4-dimethylcyclohexane | 0.52 |
| Total | 16.87 |
| MAH | |
| Benzene | 5.62 |
| Toluene | 17.74 |
| 1,3-dimethylbenzene | 6.61 |
| 1,4-dimethylbenzene | 3.03 |
| 1,2-dimethylbenzene | 2.80 |
| Ethylbenzene | 6.54 |
| n-propylbenzene | 0.29 |

TABLE 10-continued

| Component | Mass % |
|---|---|
| 1,3-methylethylbenzene | 4.40 |
| 1,4-methylethylbenzene | 2.02 |
| 1,3,5-trimethylbenzene | 0.93 |
| 1,2-methylethylbenzene | 1.07 |
| 1,2,4-trimethylbenzene | 2.24 |
| 1,2,3-trimethylbenzene | 0.31 |
| 1,3-diethylbenzene | 0.76 |
| n-butylbenzene | 0.43 |
| 1,3-dimethyl-5-ethylbenzene | 0.76 |
| 1,4,dimethyl-2-ethylbenzene | 0.35 |
| 1,3-dimethyl-4-ethylbenzene | 0.51 |
| 1,2-dimethyl-4-ethylbenzene | 0.65 |
| 1,3-methyl-n-butylbenzene | 0.59 |
| n-pentylbenzene | 0.39 |
| 1,4-methyl-n-pentylbenzene | 0.70 |
| n-hexylbenzene | 0.27 |
| Total | 59.03 |
| Heavies | |
| 2-3-dihydroindene | 0.64 |
| 5-methylindan | 0.48 |
| 4-methylindan | 0.24 |
| naphthalene | 0.27 |
| Total | 1.64 |

The overall mass balance obtained from the quantitative and qualitative measurement of feed and product composition obtained from hydrocracking Catalyst D and selective ring opening Catalyst 2A in a single reactor is presented in Table 11. Results show a hydrogen consumption of about 2.8 wt. % and increase in BTX content by about 27 wt. %.

TABLE 11

| Feed (PyOil) | wt. % | Product | wt. % |
|---|---|---|---|
| Hydrogen | 8.84 | Hydrogen | 6.06 |
| $C_{1-4}$ Hydrocarbons | 0.00 | Paraffins | |
| Benzene | 0.00 | $C_1$ | 0.01 |
| Toluene | 1.50 | $C_2$ | 0.77 |
| Xylenes | 1.11 | $C_3$ | 0.02 |
| 19Ethylbenzene | 3.12 | $C_4$ | 4.93 |
| n-Propylbenzene | 2.04 | $C_5$ | 5.00 |
| i-Propylbenzene | 0.82 | $C_{6+}$ | 6.74 |
| Ethyl toluenes | 3.85 | Cycloparaffins | |
| Cycloparaffins | 1.35 | $C_5$ | 13.27 |
| Dicyclopentadiene + derivatives thereof | 47.29 | $C_6$ | 3.85 |
| Indene + derivatives thereof | 16.85 | MAH | |
| Naphthalene + derivatives thereof | 13.25 | Benzene | 4.64 |
| Total | 100.00 | Toluene | 14.72 |
| | | Ethylbenzene | 5.44 |
| | | Xylenes | 10.32 |
| | | Ethyltoluenes | 5.35 |
| | | Trimethylbenzenes | 2.91 |
| | | $C_{10}$ aromatic hydrocarbons | 3.44 |

TABLE 11-continued

| Feed (PyOil) | wt. % | Product | wt. % |
|---|---|---|---|
| | | $C_{11}$ aromatic hydrocarbons | 1.10 |
| | | Heavies | |
| | | Indene + derivatives thereof + Naphthalene + derivatives thereof | 2.15 |
| | | Unknowns | 5.99 |
| | | Coke | 3.30 |
| | | Total | 100.00 |
| Grouped Amounts | | Grouped Amounts | |
| Hydrogen | 8.84 | Hydrogen | 6.06 |
| $C_{1-6+}$ Paraffins | 0.00 | $C_{1-6+}$ Paraffins | 17.47 |
| $C_{5-6}$ Cycloparaffins | 1.35 | $C_{5-6}$ Cycloparaffins | 17.12 |
| BTX | 2.61 | BTX | 29.68 |
| Other Aromatic hydrocarbons | 9.83 | Other Aromatic hydrocarbons | 18.23 |
| Heavies and Coke | 77.37 | Heavies and Coke | 11.44 |
| Total | 100.00 | Total | 100.00 |

The present disclosure provides that it was surprisingly found that by advantageously employing two-stage processing including hydrocracking and subsequent selective ring opening, conversion of dicyclopentadiene in a feedstock, e.g., hydrocarbon feedstock, can be improved.

This disclosure further encompasses the following aspects.

Aspect 1. A process for converting a feedstock comprising dicyclopentadiene to monoaromatic hydrocarbons, the process comprising: providing a hydrocracking catalyst comprising a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst; and contacting the feedstock with the hydrocracking catalyst in the presence of hydrogen to provide a reaction product stream comprising the monoaromatic hydrocarbons converted from the dicyclopentadiene.

Aspect 2. The process of Aspect 1, wherein the feedstock and the reaction product stream further comprise indene or a derivative thereof, naphthalene or a derivative thereof, or a combination comprising at least one of the foregoing.

Aspect 3. The process of Aspect 2, wherein a conversion of dicyclopentadiene and derivates thereof in the feedstock is greater than each of a conversion of indene and derivatives thereof in the feedstock and a conversion of naphthalene and derivatives thereof in the feedstock.

Aspect 4. The process of Aspect 2 or 3, further comprising converting dicyclopentadiene to indene or a derivative thereof, naphthalene or a derivative thereof, or a combination comprising at least one of the foregoing.

Aspect 5. The process of any one of the foregoing aspects, wherein further comprising contacting at least a portion of the reaction product stream with a selective ring opening catalyst in the presence of hydrogen in a selective ring opening reaction zone, wherein the selective ring opening catalyst comprises a zeolite support having a silica to alumina molar ratio of 25 to 100, such as 30 to 45, 33 to 42, or 35 to 40, and 0.01 to 20 weight percent, such as 0.05 to 18 weight percent or 0.1 to 15 weight percent, of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing.

Aspect 6. The process of any one of the foregoing aspects, wherein the zeolite support of the hydrocracking catalyst has a silica to alumina molar ratio of 10 to 40, such as 15 to 40 or 15 to 35.

Aspect 7. The process of any one of the foregoing aspects, wherein the zeolite support of the hydrocracking catalyst has a total pore volume of less than 0.25 $cm^3/g$.

Aspect 8. The process any one of the foregoing aspects, wherein the zeolite support of the hydrocracking catalyst comprises Y-zeolite.

Aspect 9. The process of any one of the foregoing aspects, wherein the feedstock comprises the dicyclopentadiene and derivatives thereof in an amount of greater than 35 weight percent, such as greater than 40 weight percent or greater than 45 weight percent, based on a total weight of the feedstock.

Aspect 10. The process of any one of the foregoing aspects, wherein the dicyclopentadiene is contacted with the hydrocracking catalyst in the presence of hydrogen at a pressure of 500 to 3,500 kilopascals, a temperature of 200 to 500° C., and a liquid hourly space velocity of 0.5 to 6 $hour^{-1}$, such as a pressure of 1,000 to 3,000 kilopascals, a temperature of 250 to 450° C., and a liquid hourly space velocity of 1 to 5 $hour^{-1}$, or a pressure of 1,500 to 2,500 kilopascals, a temperature of 300 to 400° C., and a liquid hourly space velocity of 2 to 4 hour-1.

Aspect 11. The process of any one of the foregoing aspects, wherein the reaction product stream comprises the dicyclopentadiene and derivatives thereof in an amount of less than 5 weight percent, such as less than 3 weight percent dicyclopentadiene or less than 1 weight percent dicyclopentadiene, based on a total weight of the reaction product stream.

Aspect 12. The process of any one of the foregoing aspects, wherein a conversion of dicyclopentadiene and derivates thereof is greater than 70 weight percent, such as greater than 75 weight percent or greater than 80 weight percent, based on a total weight of the dicyclopentadiene and derivatives thereof in the feedstock.

Aspect 13. A process for converting a feedstock comprising dicyclopentadiene to monoaromatic hydrocarbons, the process comprising contacting the feedstock with a hydrocracking catalyst in the presence of hydrogen in a hydrocracking reaction zone at a pressure of 500 to 3,500 kilopascals, a temperature of 200 to 500° C., and a liquid hourly space velocity of 0.5 to 6 hour"1, such as a pressure of 1,000 to 3,000 kilopascals, a temperature of 250 to 450° C., and a liquid hourly space velocity of 1 to 5 hour"1, or a pressure of 1,500 to 2,500 kilopascals, a temperature of 300 to 400° C., and a liquid hourly space velocity of 2 to 4 hour$^{-1}$, to convert at least a portion of the dicyclopentadiene to monoaromatic hydrocarbons, and provide an intermediate product stream comprising the monoaromatic hydrocarbons converted from the dicyclopentadiene, indene or a derivative thereof, naphthalene or a derivative thereof, or a combination comprising at least one of the foregoing, wherein the hydrocracking catalyst comprises a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst; and contacting at least a portion of the intermediate product stream with a selective ring opening catalyst in the presence of hydrogen in a selective ring opening reaction zone at a pressure of 1,000 to 15,000 kilopascals and at a temperature of 100 to 700° C., such as 3,000 to 13,000 kilopascals and 200 to 600° C. or 5,000 to 10,000 kilopascals and 300 to 500° C., to convert at least a portion of the indene or a derivative thereof, naphthalene or a derivative thereof, or a combination comprising at least one of the foregoing to additional monoaromatic hydrocarbons, wherein the selective ring opening catalyst comprises a zeolite support having a silica to alumina molar ratio of 25 to 100, such as 30 to 45, 33 to 42, or 35 to 40, and 0.01 to 20 weight percent, such as 0.05 to 18 weight percent or 0.1 to 15 weight percent, of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing.

Aspect 14. The process of Aspect 13, wherein the selective ring opening catalyst comprises ß-zeolite.

Aspect 15. The process of Aspect 13 or 14, wherein a feed to the selective ring opening reaction zone comprises dicyclopentadiene and derivatives thereof in an amount of less than 5 weight percent, such as less than 3 weight percent or less than 1 weight percent, based on a total weight of the feed to the selective ring opening reaction zone.

Aspect 16. The process of any one of Aspects 13-15, wherein (i) an overall conversion of dicyclopentadiene and derivates thereof is greater than 70 weight percent, such as greater than 80 weight percent or greater than 90 weight percent, based on a total weight of the dicyclopentadiene and derivates thereof in the feedstock;

(ii) an overall conversion of $C_{9+}$ hydrocarbons is greater than 60 weight percent, such as greater than 70 weight percent or greater than 80 weight percent, based on a total weight of the $C_{9+}$ hydrocarbons in the feedstock; or a combination comprising at least one of the foregoing.

Aspect 17. The process of Aspect 16, wherein (i) an overall yield of monoaromatic hydrocarbons is greater than 10 weight percent, such as greater than 20 weight percent or greater than 30 weight percent, calculated according to Equation 1

$$MAH\ \text{Yield}=100\times(MAH_{product}-MAH_{feedstock})/C_{9+\,feedstock} \quad \text{Equation 1}$$

wherein $MAH_{product}$ is a weight of monoaromatic hydrocarbons in the reaction product, $MAH_{feedstock}$ is a weight of monoaromatic hydrocarbons in the feedstock, and $C_{9+}$ feedstock is a weight of dicyclopentadiene and derivatives thereof, indene and derivatives thereof, and naphthalene and derivatives thereof in the feedstock;

(ii) an overall selectivity of monoaromatic hydrocarbons is greater than 25%, such as greater than 30% or greater than 35%, calculated according to Equation 2

$$MAH\ \text{Selectivity}=100\times MAH\ \text{Yield/Conversion of}\ C_{9+}\ \text{hydrocarbons} \quad \text{Equation 2}$$

wherein Conversion of $C_{9+}$ hydrocarbons is a weight percent reduction of $C_{9+}$ hydrocarbons; or a combination comprising at least one of the foregoing.

Aspect 18. The process of Aspect 16 or 17, wherein (i) an overall yield of benzene, toluene, and xylenes is greater than 15 weight percent, such as greater than 20 weight percent or greater than 25 weight percent, calculated according to Equation 3

$$BTX\ \text{Yield}=100\times(BTX_{product}-BTX_{feedstock})/C_{9+\,feedstock} \quad \text{Equation 3}$$

wherein $BTX_{product}$ is the weight of BTX in the reaction product; and

BTX feedstock is the weight of BTX in the feedstock;

(ii) an overall selectivity of benzene, toluene, and xylenes is greater than 20%, such as greater than 25% or greater than 30%, calculated according to Equation 4

$$BTX\ \text{Selectivity (\%)}=100\times BTX\ \text{Yield/Conversion of}\ C_{9+}\ \text{hydrocarbons} \quad \text{Equation 4}$$

wherein Conversion of $C_{9+}$ hydrocarbons is a weight percent reduction of $C_{9+}$ hydrocarbons; or a combination comprising at least one of the foregoing.

Aspect 19. An integrated process for converting a feedstock comprising dicyclopentadiene to monoaromatic hydrocarbons, the process comprising contacting the feedstock with a hydrocracking catalyst in the presence of hydrogen in a hydrocracking reaction zone to convert at least a portion of the dicyclopentadiene to monoaromatic hydrocarbons, and provide an intermediate product stream comprising the monoaromatic hydrocarbons converted from the dicyclopentadiene, indene or a derivative thereof, naphthalene or a derivative thereof, or a combination comprising at least one of the foregoing, wherein the hydrocracking catalyst comprises a zeolite support having an average pore diameter of 5 to 13 nanometers, such as 9 to 12 nanometers, and greater than 3 to 15 weight percent, such as 5 to 15 weight percent, of molybdenum, tungsten, nickel, cobalt, platinum, palladium, or a combination comprising at least one of the foregoing impregnated on the zeolite support, based on a total weight of the hydrocracking catalyst; and contacting at least a portion of the intermediate product stream with a selective ring opening catalyst in the presence of hydrogen in a selective ring opening reaction zone to 500° C., to convert at least a portion of the indene or a derivative thereof, naphthalene or a derivative thereof, or a combination comprising at least one of the foregoing to additional monoaromatic hydrocarbons, wherein the hydrocracking reaction zone and the selective ring opening reaction zone are within a single reactor.

Aspect 20. The integrated process of Aspect 19, wherein the selective ring opening catalyst comprises a zeolite support having a silica to alumina molar ratio of 25 to 100, such as 30 to 45, 33 to 42, or 35 to 40, and 0.01 to 20 weight percent, such as 0.05 to 18 weight percent or 0.1 to 15 weight percent, of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing.

Aspect 21. The integrated process of Aspect 19 or 20, wherein the hydrocracking reaction zone and the selective ring opening reaction zone within the single reactor are operated at a pressure of 1,000 to 15,000 kilopascals and at a temperature of 100 to 700° C., such as 3,000 to 13,000 kilopascals and 200 to 600° ° C. or 5,000 to 10,000 kilopascals and 300 to 500° C.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "aspects", "embodiments", "examples", and so forth, means that a particular element described in connection with the example is included in at least one example described herein, and may or may not be present in other examples. In addition, it is to be understood that the described elements may be combined in any suitable manner in the various aspects. The phrase "a combination thereof" or "a combination comprising at least one of the foregoing" is open-ended and includes one or more of the listed items, and can include other like items that are not listed.

Unless specified to the contrary herein, all test standards are the most recent standard in effect as of the filing date of this application, or, if priority is claimed, the filing date of the earliest priority application in which the test standard appears. Unless defined otherwise, technical and scientific terms used herein have the same meaning as is commonly understood by one of skill in the art to which this application belongs.

Compounds are described using standard nomenclature. Unless otherwise defined herein, the term "hydrocarbon" means a compound that includes carbon and hydrogen, optionally with 1 to 3 heteroatoms.

While particular aspects have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A process for converting a feedstock comprising dicyclopentadiene to monoaromatic hydrocarbons, the process comprising:

providing a hydrocracking catalyst comprising a zeolite support having an average pore diameter of 5 to 13 nanometers, and greater than 3 to 15 weight percent of at least one of molybdenum, tungsten, nickel, cobalt, platinum, palladium, and a combination thereof, comprising at least one of the foregoing impregnated on the zeolite support, based on the total weight of the hydrocracking catalyst; and contacting the feedstock with the hydrocracking catalyst in the presence of hydrogen to provide a reaction product stream comprising the monoaromatic hydrocarbons converted from the dicyclopentadiene; and contacting at least a portion of the reaction product stream with a selective ring opening catalyst in the presence of hydrogen in a selective ring opening reaction zone, wherein the feedstock comprises the dicyclopentadiene in an amount of greater than 35 weight percent, based on a total weight of the feedstock.

2. The process of claim 1, wherein the feedstock and the reaction product stream further comprise indene or a derivative thereof, naphthalene or a derivative thereof, or a combination comprising at least one of the foregoing.

3. The process of claim 1, wherein the selective ring opening catalyst comprises a zeolite support having a silica to alumina molar ratio of 25 to 100, and 0.01 to 20 weight percent of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing.

4. The process of claim 1, wherein the zeolite support of the hydrocracking catalyst has a total pore volume of less than 0.25 $cm^3/g$ and comprises Y-zeolite.

5. The process of claim 1, wherein the dicyclopentadiene is contacted with the hydrocracking catalyst in the presence of hydrogen at a pressure of 500 to 3,500 kilopascals, a temperature of 200 to 500° C., and a liquid hourly space velocity of 0.5 to 6 $hour^{-1}$.

6. The process of claim 1, wherein the reaction product stream comprises the dicyclopentadiene and derivatives thereof in an amount of less than 5 weight percent, based on a total weight of the reaction product stream.

7. The process of claim 1, wherein a conversion of dicyclopentadiene and derivates thereof is greater than 70 weight percent, based on a total weight of the dicyclopentadiene and derivatives thereof in the feedstock.

8. A process for converting a feedstock comprising dicyclopentadiene to monoaromatic hydrocarbons, the process comprising:

contacting the feedstock with a first catalyst being a hydrocracking catalyst in the presence of hydrogen in a hydrocracking reaction zone at a pressure of 500 to 3,500 kilopascals, a temperature of 200 to 500° C., and a liquid hourly space velocity of 0.5 to 6 hour 1 to convert at least a portion of the dicyclopentadiene to monoaromatic hydrocarbons, and provide an intermediate product stream comprising the monoaromatic hydrocarbons converted from the dicyclopentadiene, indene or a derivative thereof, naphthalene or a derivative thereof, or a combination comprising at least one of the foregoing, wherein the hydrocracking catalyst comprises a zeolite support having an average pore diameter of 5 to 13 nanometers, and greater than 3 to 15 weight percent of molybdenum, tungsten, nickel, cobalt, platinum, palladium, or a combination comprising at least one of the foregoing impregnated on the zeolite support, based on a total weight of the hydrocracking catalyst; and contacting at least a portion of the intermediate product stream with a second catalyst being a selective ring opening catalyst in the presence of hydrogen in a selective ring opening reaction zone at a pressure of 1,000 to 15,000 kilopascals and at a temperature of 100 to 700° C. to convert at least a portion of the indene or a derivative thereof, naphthalene or a derivative thereof, or a combination comprising at least one of the foregoing to additional monoaromatic hydrocarbons, wherein the selective ring opening catalyst comprises a zeolite support having a silica to alumina molar ratio of 25 to 100, and 0.01 to 20 weight percent of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing, wherein the feedstock comprises the dicyclopentadiene in an amount of greater than 35 weight percent, based on a total weight of the feedstock.

9. The process of claim 8, wherein the selective ring opening catalyst comprises β-zeolite.

10. The process of claim 8, wherein a feed to the selective ring opening reaction zone comprises dicyclopentadiene and derivatives thereof in an amount of less than 5 weight percent, based on a total weight of the feed to the selective ring opening reaction zone.

11. The process of claim 8, wherein (i) an overall conversion of dicyclopentadiene and derivates thereof is greater than 70 weight percent, based on a total weight of the dicyclopentadiene and derivates thereof in the feedstock;

(ii) an overall conversion of $C_{9+}$ hydrocarbons is greater than 60 weight percent, based on a total weight of the $C_{9+}$ hydrocarbons in the feedstock; or a combination comprising at least one of the foregoing.

12. The process of claim 8, wherein (i) an overall yield of monoaromatic hydrocarbons is greater than 10 weight percent, calculated according to Equation 1

$$\text{MAH Yield}=100\times(\text{MAH}_{product}-\text{MAH}_{feedstock})/C_{9+feedstock} \quad \text{Equation 1}$$

wherein $\text{MAH}_{product}$ is a weight of monoaromatic hydrocarbons in the reaction product, $\text{MAH}_{feedstock}$ is a weight of monoaromatic hydrocarbons in the feedstock, and $C_{9+\ feedstock}$ is a weight of dicyclopentadiene and derivatives thereof, indene and derivatives thereof, and naphthalene and derivatives thereof in the feedstock;

(ii) an overall selectivity of monoaromatic hydrocarbons is greater than 25%, calculated according to Equation 2

$$\text{MAH Selectivity}=100\times\text{MAH Yield/Conversion of } C_{9+} \text{ hydrocarbons} \quad \text{Equation 2}$$

wherein Conversion of $C_{9+}$ hydrocarbons is a weight percent reduction of $C_{9+}$ hydrocarbons; or a combination comprising at least one of the foregoing.

13. An integrated process for converting a feedstock comprising dicyclopentadiene to monoaromatic hydrocarbons, the process comprising:

contacting the feedstock with a first catalyst being a hydrocracking catalyst in the presence of hydrogen in a hydrocracking reaction zone to convert at least a portion of the dicyclopentadiene to monoaromatic hydrocarbons, and provide an intermediate product stream comprising the monoaromatic hydrocarbons converted from the dicyclopentadiene, indene or a derivative thereof, naphthalene or a derivative thereof, or a combination comprising at least one of the foregoing, wherein the hydrocracking catalyst comprises a zeolite support having an average pore diameter of 5 to 13 nanometers, and greater than 3 to 15 weight percent of molybdenum, tungsten, nickel, cobalt, platinum, palladium, or a combination comprising at least one of the foregoing impregnated on the zeolite support, based on a total weight of the hydrocracking catalyst; and contacting at least a portion of the intermediate product stream with a second catalyst being a selective ring opening catalyst in the presence of hydrogen in a selective ring opening reaction zone to convert at least a portion of the indene or a derivative thereof, naphthalene or a derivative thereof, or a combination comprising at least one of the foregoing to additional monoaromatic hydrocarbons, wherein the hydrocracking reaction zone and the selective ring opening reaction zone are within a single reactor, wherein the feedstock comprises the dicyclopentadiene in an amount of greater than 35 weight percent, based on a total weight of the feedstock.

14. The integrated process of claim 13, wherein the selective ring opening catalyst comprises a zeolite support having a silica to alumina molar ratio of 25 to 100, and 0.01 to 20 weight percent of a metal impregnated on the zeolite support of the selective ring opening catalyst, based on a total weight of the selective ring opening catalyst, wherein the metal comprises molybdenum, tungsten, nickel, cobalt, platinum, palladium, or a combination comprising at least one of the foregoing.

* * * * *